US009276220B2

(12) United States Patent
Kim et al.

(10) Patent No.: US 9,276,220 B2
(45) Date of Patent: Mar. 1, 2016

(54) ANTHRACENE COMPOUND AND ORGANIC LIGHT EMITTING DIODE INCLUDING THE SAME

(71) Applicant: LG DISPLAY CO., LTD., Seoul (KR)

(72) Inventors: Hyoseok Kim, Gyeonggi-do (KR); Jeongdae Seo, Incheon (KR); Eunju Jeon, Gyeonggi-do (KR); Shinhan Kim, Gyeonggi-do (KR)

(73) Assignee: LG Display Co., Ltd., Seoul (KR)

( * ) Notice: Subject to any disclaimer, the term of this patent is extended or adjusted under 35 U.S.C. 154(b) by 443 days.

(21) Appl. No.: 13/726,754

(22) Filed: Dec. 26, 2012

(65) Prior Publication Data

US 2014/0061601 A1     Mar. 6, 2014

(30) Foreign Application Priority Data

Sep. 3, 2012 (KR) ................. 10-2012-0097356

(51) Int. Cl.
| | | |
|---|---|---|
| H01L 51/54 | (2006.01) | |
| H01L 51/00 | (2006.01) | |
| C07D 401/04 | (2006.01) | |
| C07D 401/10 | (2006.01) | |
| H01L 51/50 | (2006.01) | |
| H01L 51/52 | (2006.01) | |

(52) U.S. Cl.
CPC .......... *H01L 51/0072* (2013.01); *C07D 401/04* (2013.01); *C07D 401/10* (2013.01); *H01L 51/0052* (2013.01); *H01L 51/0067* (2013.01); H01L 51/0055 (2013.01); H01L 51/0059 (2013.01); H01L 51/0081 (2013.01); H01L 51/5068 (2013.01); H01L 51/5088 (2013.01); H01L 51/5092 (2013.01); H01L 51/5278 (2013.01); H01L 2251/308 (2013.01)

(58) Field of Classification Search
CPC ............... C07D 401/04; C07D 401/10; H01L 2251/308; H01L 51/0052; H01L 51/0055; H01L 51/0059; H01L 51/0067; H01L 51/0072; H01L 51/0081; H01L 51/5068; H01L 51/5088; H01L 51/5092; H01L 51/5278
See application file for complete search history.

(56) References Cited

U.S. PATENT DOCUMENTS

| | | | |
|---|---|---|---|
| 2004/0076853 A1* | 4/2004 | Jarikov ......................... | 428/690 |
| 2007/0046189 A1* | 3/2007 | Hatwar et al. ................ | 313/506 |
| 2007/0126347 A1* | 6/2007 | Jarikov et al. ................ | 313/506 |
| 2007/0231596 A1* | 10/2007 | Spindler et al. .............. | 428/690 |
| 2009/0166670 A1* | 7/2009 | Park et al. .................... | 257/103 |

FOREIGN PATENT DOCUMENTS

| | | | |
|---|---|---|---|
| KR | 2009-029111 | * | 3/2009 |
| KR | 10-2009-0086015 A | | 8/2009 |
| WO | 2007/130263 A1 | | 11/2007 |

OTHER PUBLICATIONS

Machine translation for KR 10-2009-029111, publication date Mar. 2009.*
Office Action dated Jan. 14, 2015 for Chinese patent application No. 201210596401.9.
2nd Notification of Office Action issued Jul. 21, 2015 by the State Intellectual Property Office of China in corresponding Chinese Patent Application No. 201210596401.9, including an English language translation.

* cited by examiner

*Primary Examiner* — Dawn L. Garrett
(74) *Attorney, Agent, or Firm* — Morgan, Lewis & Bockius LLP

(57) ABSTRACT

An anthracene compound and organic light emitting diode including the same are disclosed. The organic light emitting diode includes, at least two stacks formed between a first electrode and a second electrode and a charge generation layer (CGL) including an N-type CGL and a P-type CGL formed between the stacks, wherein the N-type CGL is formed of the anthracene compound.

7 Claims, 3 Drawing Sheets

ANTHRACENE COMPOUND AND ORGANIC LIGHT EMITTING DIODE INCLUDING THE SAME

This application claims the benefit of Korean Patent Application No. 10-2012-0097356 filed on Sep. 3, 2012, which is incorporated herein by reference for all purposes as if fully set forth herein.

BACKGROUND OF INVENTION

1. Field of the Invention

This document relates to an organic light emitting diode (OLED), and more particularly, to an organic light emitting diode (OLED) including an anthracene compound.

2. Discussion of the Related Art

Recently, the importance of flat panel displays (FPD) is increasing with the development of multimedia. Therefore, various displays such as liquid crystal displays (LCD), plasma display panels (PDP), field emission displays (FED), and organic light emitting diodes (OLED) are commercialized.

In particular, an OLED has high response speed of no more than 1 ms, uses a small amount of power, and is self-emissive. In addition, since there is no problem in a viewing angle, the OLED is advantageous as a moving picture display medium regardless of the size of an apparatus. In addition, since the OLED may be manufactured at a low temperature and has simple manufacturing processes based on a conventional semiconductor process technology, the OLED is spotlighted as a next generation FPD.

The OLED includes a light emitting layer between an anode electrode and a cathode electrode so that holes supplied from the anode electrode and electrons supplied from the cathode electrode are combined with each other in the light emitting layer to form excitons that are pairs of holes and electrons. Light is emitted by energy generated by the excitons returning to a ground state.

The OLED is developed to have various structures. Among them, a tandem-type OLED in which a number of light emitting layers are laminated is developed. The tandem-type OLED has a structure in which a plurality of stacks each formed of a hole injection layer (HIL)/a hole transport layer (HTL)/a light emitting layer/an electron transport layer (ETL)/an electron injection layer (EIL) are laminated between the anode electrode and the cathode electrode. In particular, a charge generation layer (CGL) formed of an N-type CGL and a P-type CGL is provided between the stacks to generate charges or to inject charges into the light emitting layers.

However, in the CGL, due to a difference in an energy level between the N-type CGL and the P-type CGL, a characteristic in which electrons generated in an interface between the P-type CGL and an adjacent hole injection layer by charge generation are injected into the N-type CGL is deteriorated. In addition, when the conventional N-type CGL is doped with an alkali metal, the alkali metal is diffused into the P-type CGL so that the life of the OLED is reduced.

SUMMARY

The present invention has been made in an effort to provide an anthracene compound and an organic light emitting diode (OLED) including the same in which a new N-type CGL is provided so that the driving voltage of the OLED is reduced, that the emission efficiency of the OLED is improved, and that the life of the OLED is increased.

In one aspect, there is An anthracene compound represented by formula 1,

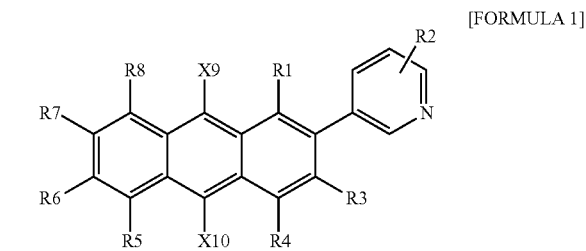

[FORMULA 1]

wherein each of R1 to R8 is one selected from the group consisting of a hydrogen-containing alkyl or heteroalkyl group having 1 to 20 carbon atoms, an aryl group having 5 to 20 carbon atoms, and a nitrogen, sulfur, or oxygen-containing heteroaryl group having 4 to 20 carbon atoms, and wherein each of X9 and X10 is one selected from the group consisting of a nitrogen, sulfur, or oxygen-containing heteroaryl group having 4 to 20 carbon atoms and an aryl group having 6 to 20 carbon atoms.

In another aspect, there is an organic light emitting diode (OLED) includes at least two stacks formed between a first electrode and a second electrode and a charge generation layer (CGL) including an N-type CGL and a P-type CGL formed between the stacks, wherein the N-type CGL is formed of the anthracene compound.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings.

DETAILED DESCRIPTION

Reference will now be made in detail to embodiments of the invention, examples of which are illustrated in the accompanying drawings. Wherever possible, the same reference numbers will be used throughout the drawings to refer to the same or like parts. It will be paid attention that detailed description of known arts will be omitted if it is determined that the arts can mislead the embodiments of the invention.

Figure 1:
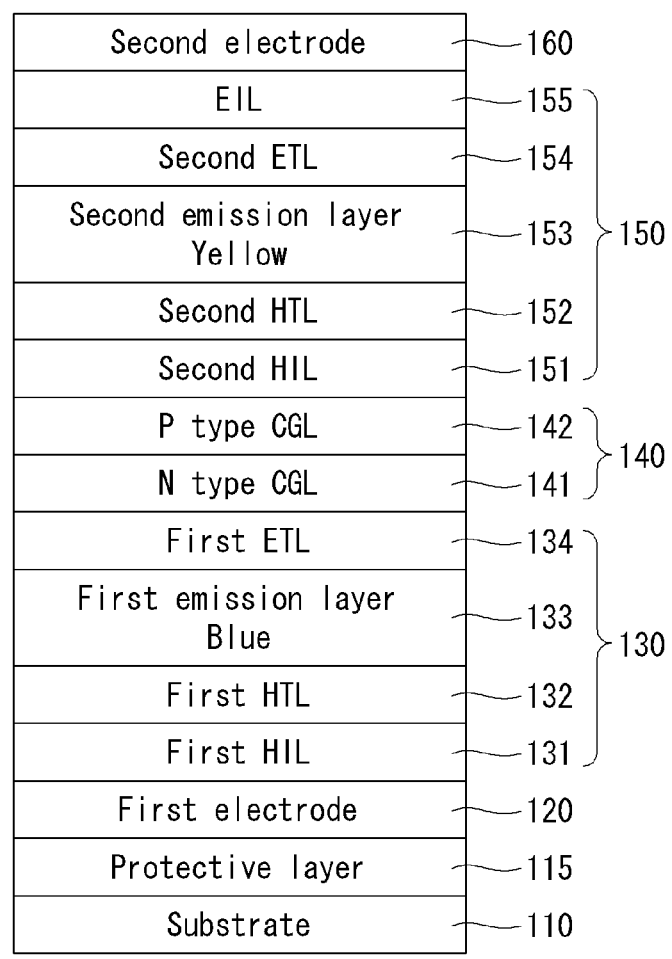
FIG. 1 is a view illustrating an organic light emitting diode (OLED) according to an embodiment of the present invention.

FIG. 1 is a view illustrating an organic light emitting diode (OLED) according to an embodiment of the present invention. Hereinafter, an OLED in which two stacks are laminated will be taken as an example. However, the present invention is not limited to the above.

Referring to FIG. 1, an OLED 100 according to an embodiment of the present invention may be a white OLED including yellow light and blue light. In detail, the OLED 100 includes a first electrode 120 positioned on a substrate 110, a first stack 130 positioned on the first electrode 120 and including a first light emitting layer 133, a charge generation layer (CGL) 140 positioned on the first stack 130, a second stack 150 positioned on the CGL 140 and including a second light emitting layer 153, and a second electrode 160 positioned on the second stack 150.

The substrate 110 may be formed of transparent glass, plastic, or a conductive material. The first electrode 120 as an anode electrode for injecting holes may be a transparent electrode that transmits light. The first electrode 120 is formed of one of indium tin oxide (ITO), indium zinc oxide (IZO), and zinc oxide (ZnO). A reflecting layer 115 may be further provided between the substrate 110 and the first electrode 120. The reflecting layer 115 for reflecting light upward may be formed of one of Al, Ag, and Ni under the first electrode 120.

The first stack 130 positioned on the first electrode 120 may include the first light emitting layer 133 for emitting blue light. In the first stack 130, since only a blue light emitting layer is included as the first light emitting layer 133 so that only blue light is emitted, stability of blue may be improved. In the first light emitting layer 133 for emitting blue light, fluorescent blue dopant may be mixed with one host. For example, in the first light emitting layer 133, fluorescent blue dopant such as 1,6-Bis(diphenylamine)pyrene or TBPe(tetrakis(t-butyl)perylene) may be mixed with a host material such as AND(9,10-di(2-naphthyl)anthracene) or DPVBi(4,4'-bis(2,2-diphenylethen-1-yl)-diphenyl). In addition, the fluorescent blue dopant may be deep blue dopant or sky blue dopant. The deep blue dopant may be 4'-N,N-diphenylaminostyryl-triphenyl(DPA-TP), 2,5,2',5'-tetrastyryl-biphenyl (TSB), or an anthracene derivative. The sky blue dopant may be p-bis(p-N,N-diphenyl-aminostyryl)benzene or phenylcyclopentadiene.

The first stack 130 may further include a first hole injection layer 131 and a first hole transport layer 132 formed between the first electrode 120 and the first light emitting layer 133 and a first electron transport layer 134 formed between the first light emitting layer 133 and the CGL 140.

The hole injection layer 131 for smoothly injecting holes from the first electrode 120 to the first light emitting layer 133 may be formed of at least one selected from the group consisting of cupper phthalocyanine (CuPc), poly(3,4)-ethylenedioxythiophene (PEDOT), polyaniline (PANI), and N,N-dinaphthyl-N,N'-diphenyl benzidine (NPD). However, the present invention is not limited to the above.

The first hole transport layer 132 for smoothly transporting holes may be formed of at least one selected from the group consisting of N,N-dinaphthyl-N,N'-diphenyl benzidine (NPD), N,N'-bis-(3-methylphenyl)-N,N'-bis-(phenyl)-benzidine (TPD), s-TAD, and 4,4',4''-Tris(N-3-methylphenyl-N-phenyl-amino)-triphenylamine (MTDATA). However, the present invention is not limited to the above.

The first electron transport layer 134 for smoothly transporting electrons may be formed of at least one selected from the group consisting of Alq3(tris(8-hydroxyquinolino)aluminum), PDB, TAZ, Spiro-PBD, BAlq, and SAlq. However, the present invention is not limited to the above.

On the other hand, the CGL 140 positioned on the first stack 130 is a PN conjunction CGL in which an N-type CGL 141 and a P-type CGL 142 are in conjunction with each other. The PN conjunction CGL 140 generates charges or divides charges into holes and electrons to inject charges into the light emitting layers. That is, the N-type CGL 141 supplies electrons to the first light emitting layer 133 adjacent to the first electrode and the P-type CGL 142 supplies holes to the second light emitting layer 153 adjacent to the second electrode 160 so that the emission efficiency of the OLED including a plurality of light emitting layers may be increased and that the driving voltage of the OLED may be reduced.

The N-type CGL 141 is formed of an anthracene compound and will be described in detail later. The P-type CGL 142 may be formed of an organic material doped with a metal or P-type dopant. Here, the metal may be formed of one or at least two alloys selected from the group consisting of Al, Cu, Fe, Pb, Zn, Au, Pt, W, In, Mo, Ni, and Ti. In addition, the P-type dopant used for the organic material doped with the P-type dopant and a host may be formed of commonly used materials. For example, the P-type dopant may be one material selected from the group consisting of 2,3,5,6-thetraflu-ore-7,7,8,8-tetracyanoquinodimethane (F4-TCNQ), a derivative of tetracyanoquinodimethane, iodine, FeCl3, FeF3, and SbCl5. The host may be one material selected from the group consisting of N,N'-di(naphthalene-1-i1)-N,N-diphenyl-benzidine (NPB), N,N'-diphenyl-N,N'-bis(3-methylphenyl)-1,1-biphenyl-4,4'-diamine (TPD), and N,N',N'-tetranaphthyl-benzidine (TNB).

On the other hand, the second stack 150 positioned on the CGL 140 may include the second light emitting layer 153 for emitting yellow light. In the second light emitting layer 153, yellow dopant may be included in a host or red and green dopants may be included in one host.

For example, when the yellow dopant is included in the host in the second light emitting layer 153, the same material as the above-described host of the first light emitting layer 133 may be used as the host and the blue dopant and Irpq2acac (bis(phenylquinoline) iridium acetylacetonate) may be used as yellow phosphor dopant. When the red and green dopants are included in one host in the second light emitting layer 153, Ir(piq)2acac (bis(phenylisoquinoline) iridium acetylacetonate) may be used as red phosphor dopant included in the host and Irppy3(tris(phenylpyridine)iridium) may be used as green phosphor dopant.

The second stack 150 further includes a second hole injection layer 151 and a second hole transport layer 152 formed between the CGL 140 and the second light emitting layer 153 and a second electron transport layer 154 and an electron injection layer 155 formed between the second light emitting layer 153 and the second electrode 160. The second hole injection layer 151, the second hole transport layer 152, and the second electron transport layer 154 are the same as the above-described first hole injection layer 131, first hole transport layer 132, and first electron transport layer 134 and description thereof will be omitted.

The electron injection layer 155 for smoothly injecting electrons may be formed of at least one selected from the group consisting of Alq3(tris(8-hydroxyquinolino)aluminum), PBD, TAZ, Spiro-PBD, BAlq, or SAlq. However, the present invention is not limited to the above. In addition, the electron injection layer 155 may be a metal halide compound, for example, at least one selected from the group consisting of $MgF_2$, LiF, NaF, KF, RbF, CsF, FrF, and $CaF_2$. However, the present invention is not limited to the above.

The second electrode (cathode) 160 may be formed of a transparent material so that light emitted from the light emitting layers 133 and 153 may be emitted to the entire surface. For example, the second electrode 160 may be one of ITO, IZO, and ZnO.

The N-type CGL 141 according to the present invention is formed of the anthracene compound represented by the formula 1.

[FORMULA 1]

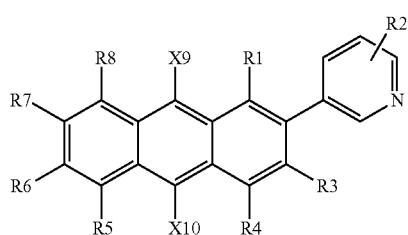

In the formula 1, each of R1 to R8 is one selected from a hydrogen-containing alkyl or heteroalkyl group having 1 to 20 carbon atoms, an aryl group having 5 to 20 carbon atoms, and a nitrogen, sulfur, or oxygen-containing heteroaryl group having 4 to 20 carbon atoms and each of X9 and X10 is one selected from a nitrogen, sulfur, or oxygen-containing heteroaryl group having 4 to 20 carbon atoms and an aryl group having 6 to 20 carbon atoms.

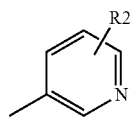

is one selected from the group consisting of

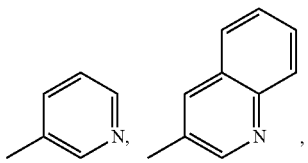

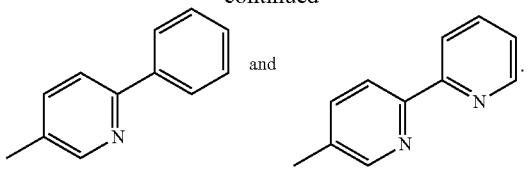

R6 is one selected from the group consisting of hydrogen,

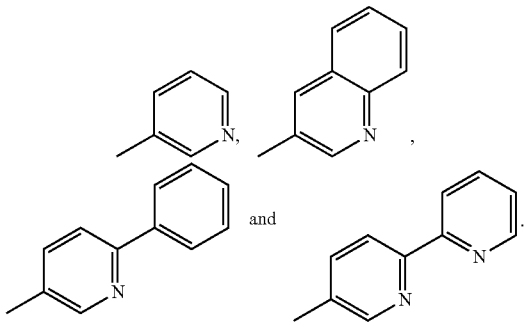

For example, the anthracene compound represented by the formula 1 may be formed of the following compounds NC01 to NC20 through various combinations of

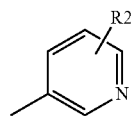

and R6 as illustrated in the table 1.

TABLE 1

| R6 |  | | | |
|---|---|---|---|---|
| —H | NC01 | NC02 | NC03 | NC04 |
| (3-pyridyl) | NC05 | NC06 | NC07 | NC08 |
| (quinolinyl) | NC09 | NC10 | NC11 | NC12 |

TABLE 1-continued

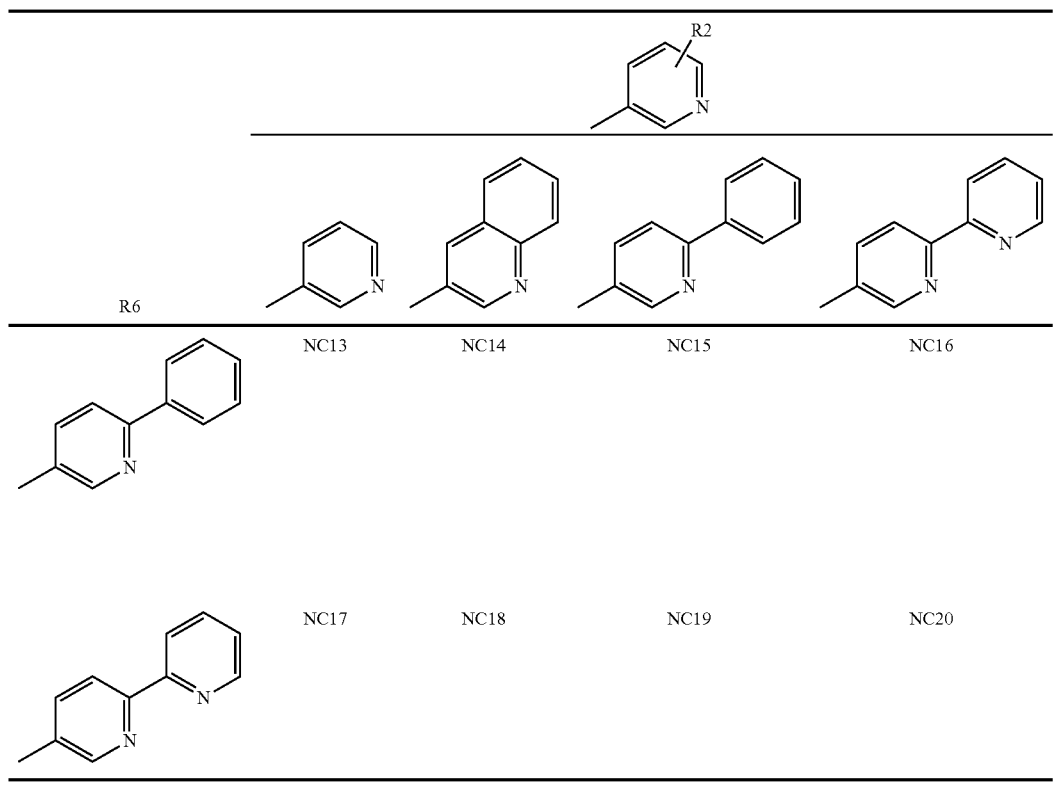

| NC13 | NC14 | NC15 | NC16 |
| NC17 | NC18 | NC19 | NC20 |

The anthracene compound according to the present invention may be doped with an alkali metal. Therefore, as illustrated in formula 2, since SP2-nitrogen of the anthracene compound is a reactive site having relatively abundant electrons, SP2-nitrogen is bonded with Li to form a gap state. Electrons may be easily transported from the P-type CGL to the N-type CGL by the formed gap state.

[FORMULA 2]

Therefore, the alkali metal doped on the conventional N-type CGL is diffused into the P-type CGL to prevent the life from being reduced and to easily transport electrons.

Hereinafter, a composition example of the anthracene compound used for the N-type CGL according to the present invention and an OLED including the compound will be described in detail with reference to the following composition example and the embodiment. The following embodiment is only an embodiment and the present invention is not limited to the following embodiment.

COMPOSITION EXAMPLE 1) composition of 2,6-dibromo-9,10-diphenylanthracene

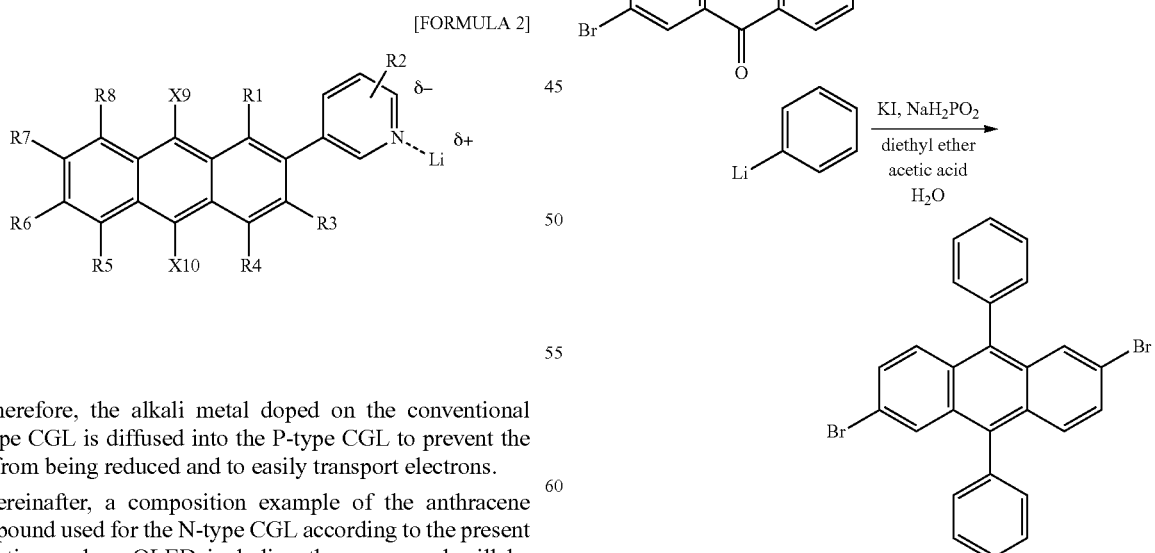

While agitating solution manufactured by dissolving 2,6-dibromoantraquinon (3 g, 8.2 mmol) in ethylether (Et20), solution manufactured by dissolving phenyllithium (2 g, 23.8 mmol) in ethylether (Et20) is slowly dropped. At this time, reaction is performed in a dry ice tub. Then, when temperature is raised to the room temperature, an intermediate is obtained. Solid obtained by filtering the intermediate is dissolved in acetic acid of 60 mL. Then, KI and NaH$_2$PO$_2$ are put into the solution obtained by dissolving the intermediate in acetic acid. Then, the solution is refluxed at 130° C. for 24 hours. When the reaction is completed, water is put and filtering is performed. Then, a generated solid material is re-crystallized using methylene chloride and methanol to obtain 2,6-dibromo-9,10-diphenylanthracene (2.7 g, 5.5 mmol, 67%).

2) manufacturing of NC05

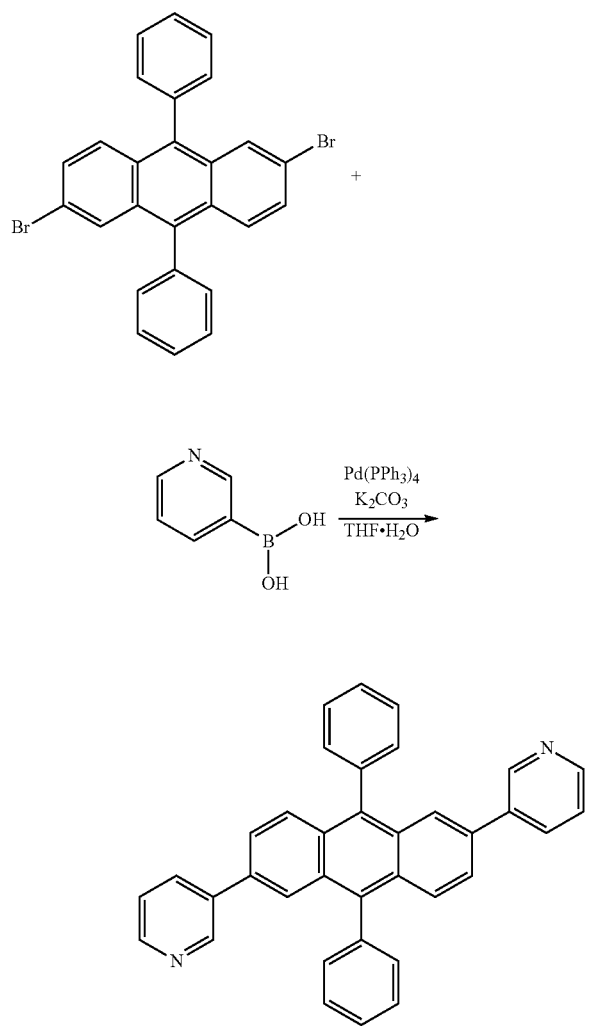

Pyridine boric acid (2.5 g, 20.3 mmol) and anhydrous tetrahydrofuran of 60 ml are put into the composed 2,6-dibromo-9,10-diphenylanthracene (3 g, 6.1 mmol) and the resultant solution is agitated. tetrakis(triphenylphosphine)palladium(1.4 g, 1.2 mmol), potassium carbonate (K$_2$CO$_3$, 6.3 g, 24.6 mmol), and distilled water of 60 mL are put and the resultant solution is refluxed at 100° C. for 24 hours. When reaction is completed, after removing tetrahydrofuran, a generated solid material is filtered. The solid material is re-crystallized using dichloromethane and methanol to obtain 2,6-dipyridine-9,10-diphenylanthracene, NC05) (2.0 g, 4.1 mmol, 67%).

3) manufacturing of NC10

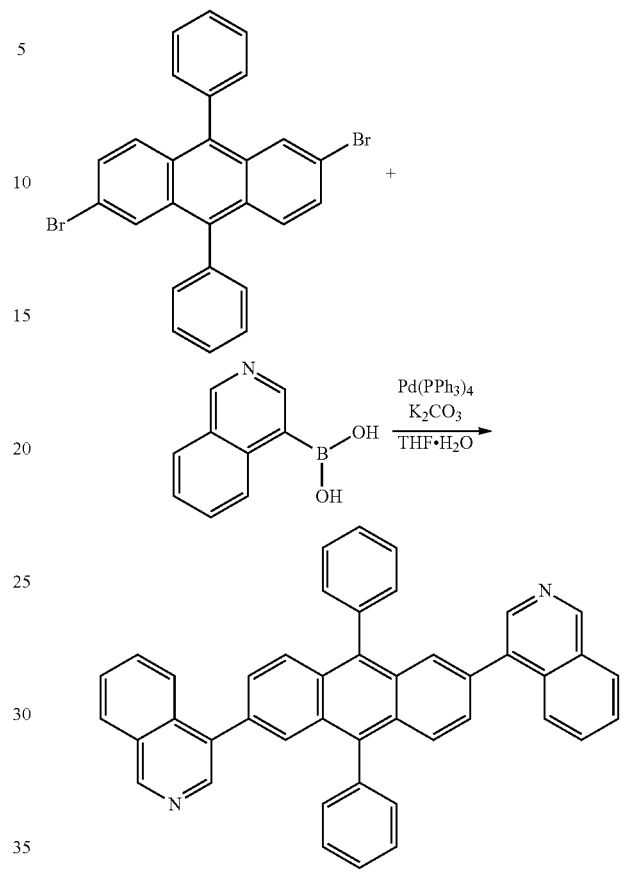

Quinoline boric acid (3.5 g, 20.2 mmol) and anhydrous tetrahydrofuran of 60 ml are put into the composed 2,6-dibromo-9,10-diphenylanthracene (3 g, 6.1 mmol) and the resultant solution is agitated. tetrakis(triphenylphosphine)palladium(1.4 g, 1.2 mmol), potassium carbonate (K$_2$CO$_3$, 6.3 g, 24.6 mmol), and distilled water of 60 mL are put and the resultant solution is refluxed at 100° C. for 24 hours. When reaction is completed, after removing tetrahydrofuran, a generated solid material is filtered. The solid material is re-crystallized using dichloromethane and methanol to obtain 2,6-diquinoline-9,10-diphenylanthracene, NC10) (2.0 g, 4.3 mmol, 69%).

Embodiment

Hereinafter, an embodiment in which the anthracene compounds represented as NC05 and NC10 manufactured in the above-described composition examples are used as the N-type CGL to manufacture the OLED is disclosed.

Embodiment 1

After patterning ITO glass so that the emission area of the ITO glass is 2 mm×2 mm, the ITO glass is washed. After mounting a substrate in a vacuum chamber, base pressure is made to be 1×10$^{-6}$ torr. Then, HAT-CN as a hole injection layer is deposited on ITO as an anode to a thickness of 50 Å. Then, N,N'-diphenyl-N,N'-bis-[4-(phenyl-m-tolylamino)-phenyl-]-biphenyl-4,4'-diamine (DNTPD) of within 10% is doped on 4,4'-bis[N-(1-naphthyl)-N-phenylamino]-biphenyl (NPD) as a hole transport layer and is deposited to a thickness of 1,500 Å. Then, TCTA is continuously deposited to a thickness of 200 Å. Then, a light emitting layer where tBu-Perylene dopant is included in ADN host is formed to a thickness of 250 Å. Then, Alq3 as an electron transport layer is formed to a thickness of 250 Å. Then, Li that is an alkali metal is doped on a material represented as NC05 so that an N-type CGL is formed to a thickness of 100 Å. HAT-CN as a P-type CGL is formed to a thickness of 100 Å. Al as a cathode is formed to a thickness of about 1,000 Å so that an OLED is manufactured.

-continued

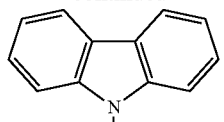
<TCTA>

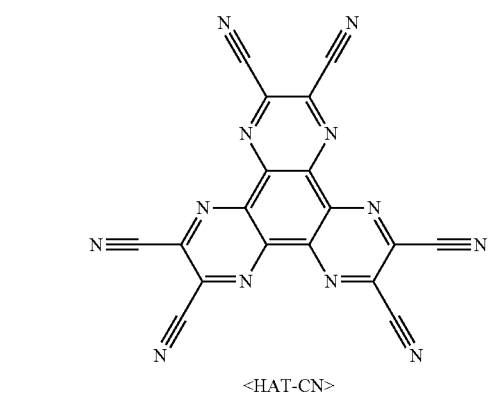
<HAT-CN>

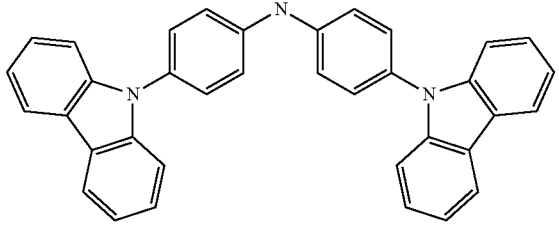
<ADN>

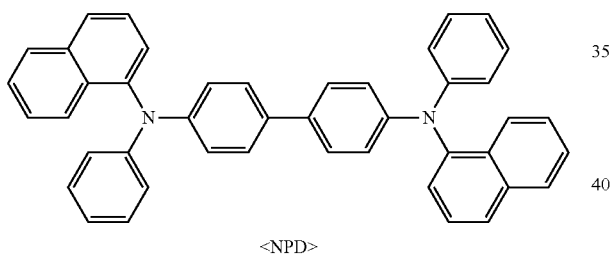
<NPD>

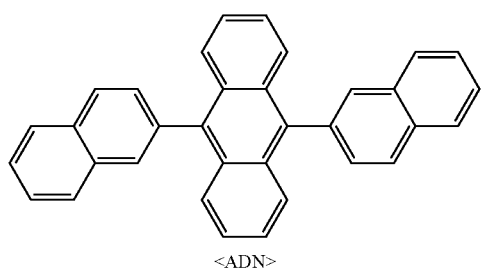
<tBu-Pyrylene>

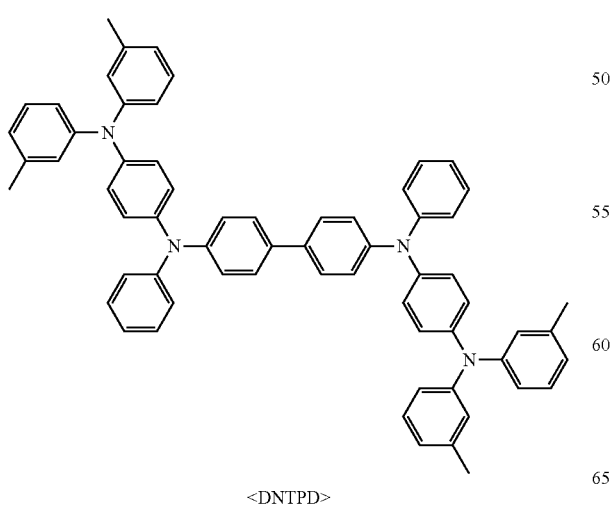
<DNTPD>

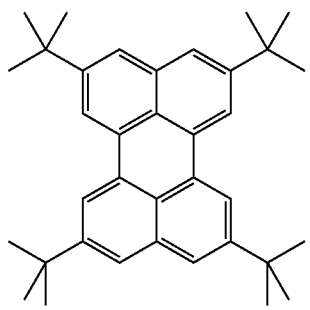
<Alq3>

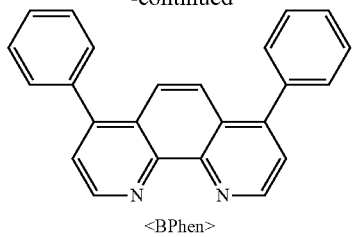

<BPhen>

Embodiment 2

Under the same condition as the above-described embodiment 1, the compound represented as NC10 is used as the material of an N-type CGL to manufacture an OLED.

COMPARATIVE EXAMPLE

Under the same condition as the above-described embodiment 1, the following Bphen material is used as the material of an N-type CGL to manufacture an OLED.

Figure 2:
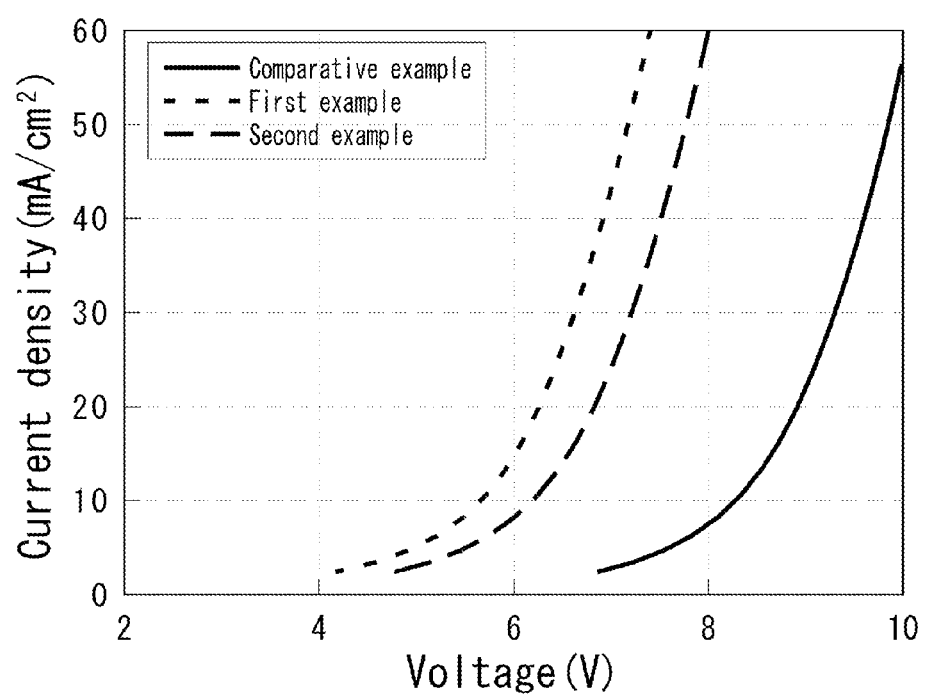
FIG. 2 is a graph illustrating current density in accordance with the driving voltage of the OLED manufactured in accordance with the embodiment of the present invention.
Figure 3:
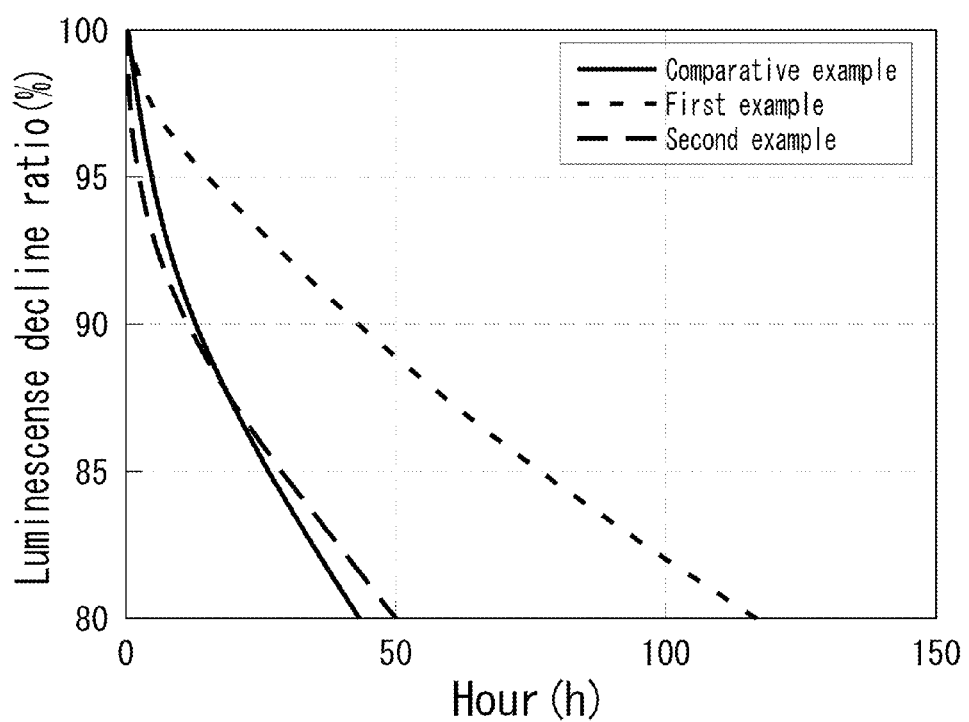
FIG. 3 is a graph illustrating a life reduction ratio in accordance with time of the OLED manufactured in accordance with the embodiment of the present invention.

The driving voltages, the current efficiencies, the quantum efficiencies, the color coordinates, and the lives of the OLEDs manufactured in accordance with the above embodiments 1 and 2 and comparative example are measured to be illustrated in the following table 2. In addition, current densities in accordance with the driving voltages are measured to be illustrated in FIG. 2 and brightness reduction ratios in accordance with time are measured to be illustrated in FIG. 3.

TALBE 2

| | Driving voltage (V) | Current efficiency (cd/A) | Quantum efficiency (%) | Color coordinates | | Life (T80, hr) |
|---|---|---|---|---|---|---|
| | | | | CIE x | CIE y | |
| Embodiment 1 | 5.4 | 7.2 | 8.1 | 0.135 | 0.101 | 110 |
| Embodiment 2 | 6.2 | 6.5 | 7.3 | 0.134 | 0.102 | 50 |
| Comparative example | 8.3 | 5.6 | 5.8 | 0.134 | 0.111 | 43 |

As illustrated in the table 1, it is noted that the OLEDs manufactured in accordance with the embodiments 1 and 2 according to the present invention have higher color coordinates than the comparative example and that the driving voltages, the current efficiencies, and the quantum efficiencies of the OLEDs are remarkably improved. In particular, referring to FIG. 2, the current densities in accordance with the driving voltages are improved and, referring to FIG. 3, the lives are remarkably increased.

Therefore, in the anthracene compound according to the embodiment of the present invention and the OLED including the same, a driving voltage, current efficiency, quantum efficiency, color coordinates, and a life are improved in comparison with the conventional OLED.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An organic light emitting diode (OLED), comprising:
   at least two stacks formed between a first electrode and a second electrode; and
   a charge generation layer (CGL) including an N-type CGL and a P-type CGL formed between the stacks,
   wherein the N-type CGL comprises an anthracene compound represented by Formula 1

[FORMULA 1]

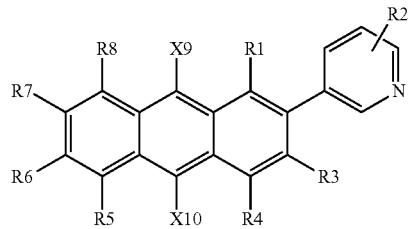

wherein:

each of R1, R3, R4, R5, R7 and R8 is one selected from the group consisting of hydrogen, an alkyl or heteroalkyl group having 1 to 20 carbon atoms, an aryl group having 5 to 20 carbon atoms, and a nitrogen, sulfur, or oxygen-containing heteroaryl group having 4 to 20 carbon atoms;

each of R2 and R6 is one selected from the group consisting of hydrogen, an alkyl or heteroalkl group having 1 to 20 carbon atoms, an aryl group havin 5 to 20 carbon atoms, and a nitrogen- or oxygen-containing heteroaryl group having 4 to 20 carbon atoms; and each of X9 and X10 is one selected from the group consisting of a nitrogen, sulfur, or oxygen-containing heteroaryl group having 4 to 20 carbon atoms and an aryl group having 6 to 20 carbon atoms.

2. The OLED of claim 1, wherein

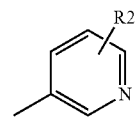

is one selected from the group consisting of

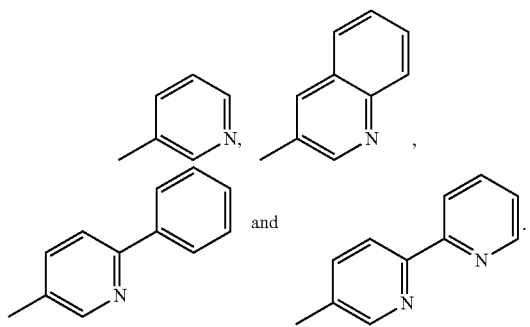

3. The OLED of claim 1, wherein R6 is one selected from the group consisting of hydrogen,

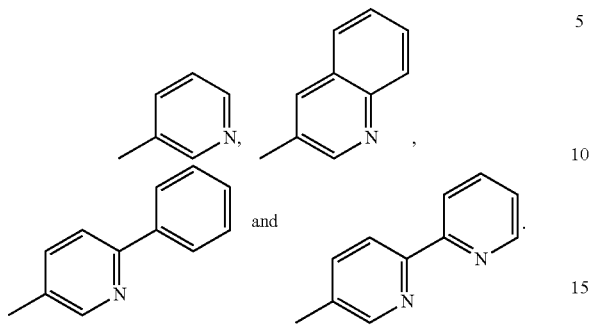

4. The OLED of claim 1, wherein each of the stacks comprises a hole injection layer (HIL) and a hole transport layer (HTL) formed on one side with a light emitting layer interposed and an electron transport layer (ETL) formed on the other side.

5. The OLED of claim 4, wherein the stacks adjacent to the second electrode further comprise electron injection layers (EIL).

6. The OLED of claim 1, wherein light emitting layers of the stacks emit light components of different colors.

7. The OLED of claim 1, wherein the N-type CGL is doped with an alkali metal.

* * * * *